United States Patent [19]

Kasai et al.

[11] Patent Number: 5,776,766
[45] Date of Patent: Jul. 7, 1998

[54] OPTICAL RESOLUTION OF CHLOROHYDRIN WITH MICROORGANISM

[75] Inventors: Naoya Kasai; Toshio Suzuki, both of Osaka-fu; Hideaki Idogaki, Hyogo-ken, all of Japan

[73] Assignee: Daiso Co., Ltd., Osaka, Japan

[21] Appl. No.: 651,935

[22] Filed: May 21, 1996

[30] Foreign Application Priority Data

May 29, 1995 [JP] Japan .................................. 7-130182

[51] Int. Cl.$^6$ ...................................................... C12P 41/00
[52] U.S. Cl. ........................ 435/280; 435/132; 435/155; 435/158
[58] Field of Search ................................. 435/280, 128, 435/134, 135, 155, 142, 145, 146, 157, 158

[56] References Cited

U.S. PATENT DOCUMENTS 5,155,043  10/1992  Murakami et al. .................. 435/280

FOREIGN PATENT DOCUMENTS

| 0 224 246 | 6/1987 | European Pat. Off. ............. 435/280 |
| 0 286 059 | 10/1988 | European Pat. Off. ............. 435/280 |
| 0 606 899 | 7/1994 | European Pat. Off. . |
| 1-247100 | 10/1989 | Japan ............................. 435/280 |
| 4-166097 | 6/1992 | Japan . |
| 4-197197 | 7/1992 | Japan . |
| 6-197790 | 7/1994 | Japan . |
| 7-147993 | 6/1995 | Japan . |

OTHER PUBLICATIONS

*Agric. Biol. Chem.*, vol. 50, No. 2, pp. 375–380, *Japan*, 1986.

*Primary Examiner*—William H. Beisner
*Attorney, Agent, or Firm*—Jacobson, Price, Holman & Stern, PLLC

[57] ABSTRACT

A novel method for preparing optically active chlorohydrin compound and optically active 1,2-diol compound and/or optically active 3-hydroxy-γ-butyrolactone which are useful as intermediates for preparing medicaments, agricultural chemicals, physiologically active substances and ferroelectric liquid crystals, which comprises treating a racemic chlorohydrin compound having the formula:

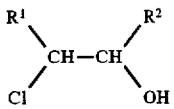

(wherein $R^1$ is H or lower alkyl group; and $R^2$ is substituted or unsubstituted lower alkyl group when $R^1$ is H; or $R^2$ is H when $R^1$ is lower alkyl group) with a microorganism, whereby selectively degrading only one of optical isomers thereof, and recovering the remaining an other optically active chlorohydrin and isolating optically active 1,2-diol compound and/or optically active 3-hydroxy-γ-butyrolactone converted by the reaction.

16 Claims, No Drawings

OPTICAL RESOLUTION OF CHLOROHYDRIN WITH MICROORGANISM

TECHNICAL FIELD

This invention relates to an optical resolution of a chlorohydrin compound with an microorganism. More particularly, it relates to a process for the production of an optically active chlorohydrin compound from the corresponding racemic compound by a biological optical resolution using a microorganism, said optically active chlorohydrin compound being useful as an chiral building block and an intermediate for the production of optically active compounds having various utilities, such as medicaments, agricultural chemicals, physiologically active substances and ferroelectric liquid crystals.

This invention provides also a process for the production of an optically active 1,2-diol compound and/or an optically active 3-hydroxy-γ-butyrolactone in addition to the optically active chlorohydrin compound by the biological optical resolution of a racemic chlorohydrin compound, wherein the production of said other compounds depends on the kinds of the microorganism used as well as the kinds of the substituent of the starting chlorohydrin compound.

PRIOR ART

Optically active compounds have usually been produced by a chemical synthesis comprising converting the corresponding optically active starting compound into the desired compound, or by an optical resolution comprising treating the corresponding racemic compound with an optically resolving agent, but recently, it is reported to produce the optically active compound by a biological optical resolution utilizing an asymmetric reduction or asymmetric hydrolysis of a racemic compound with a microorganism or an enzyme.

For example, there is reported a process of an asymmetric reduction of a β-keto ester with a microbial cell or an enzyme, specifically an asymmetric reduction of a 4-chloroacetoacetate with a baker's yeast to give an optically active 4-chloro-3-hydroxybutyrate (cf. C. J. Sih et al., Ann. N.Y. Acad. Sci., Vol. 434, pp. 186–193, 1984; C. J. Sih, BE 898386). Santaniello et al. have reported a process for the production of ethyl 4-chloro-3-hydroxybutyrate by an asymmetric reduction of ethyl 4-chloro-3-oxobutyrate with a baker's yeast (cf. E. Santaniello et al., J. Chem. Research (S), pp. 132–133, 1984). Takahashi et al. have also reported a process for the production of an optically active ethyl 4-chloro-3-hydroxybutyrate by an asymmetric reduction of ethyl 4-chloro-3-oxobutyrate with a microorganism (cf. JP-A-61-146191). As a process using an enzyme, J. Peters et al. have reported a process for the production of (S)-methyl 3-hydroxybutyrate and (R)-ethyl 4-chloro-3-hydroxybutyrate by an asymmetric reduction of methyl 3-oxobutyrate or ethyl 4-chloro-3-oxobutyrate using a carbonyl reductase produced by Rhodococcus erythropolis (cf. J. Peters et al., Appl. Microbiol. Biotechnol., Vol. 38, pp. 334–340, 1992; T. Zelinski et al., J. Biotechnol., Vol. 33, pp. 283–292, 1994). Besides, Shimizu et al. have reported a process for the production of (R)-ethyl 4-chloro-3-hydroxybutyrate by an asymmetric reduction using an aldehyde reductase produced by Sporoboromyces salmonicolor AKU 4429 (cf. S. Shimizu et al., Biotechnol. Lett. Vol. 12, No. 8, pp. 593–596, 1990; Appl. Environ. Microbiol., Vol. 56, No. 8, pp. 2374–2377, 1990).

However, according to these processes for the production of an optically active β-hydroxy ester compound from a prochiral β-keto ester compound by an asymmetric reduction using a microorganism or an enzyme, it is required to use very expensive coenzymes such as NADH (nicotinamide adenine dinucleotide) or NADPH (nicotinamide adenine dinucleotide phasphate), and further required to use additionally an enzyme such as glucose oxidase or formic acid dehydrogenase because of necessity of a reaction for converting again to the reduced form from the oxidized form. Moreover, the rate of reaction is determined based on the said reaction for converting the reduced form from the oxidized form. Thus, these known processes are not necessarily satisfactory from the industrial viewpoint.

Nakamura et al. have reported a process for the production of (R)-4-chloro-3-hydroxybutyronitrile by using 1,3-dichloro-2-propanol or epichlorohydrin as a substrate, and treating the substrate with a dehydrogenase produced by Corynebacterium sp. N-1074 in the presence of KCN (cf. JP-A-3-53889, JP-A-3-53890). It is also reported to obtain an optically active 4-chloro-3-hydroxybutyronitrile or the corresponding ester by treating a recemic 4-chloro-3-hydroxybutyronitrile with a lipase in the presence of a fatty acid ester (cf. JP-A-2-27995). However, the optically active products obtained by these processes have low optical purity, and hence, are not suitable as an industrial process.

Further, Lee et al. have reported a process for the production of (R)-1,2-propanediol compound and (R)-1,2-butanediol compound by the reduction of 1-hydroxy-2-propanone and 1-hydroxy-2-butanone with a glycerol dehydrogenase, respectively [cf. L. G. Lee, G. M. Whitesides, J. Org. Chem., Vol. 51, pp. 25–36 (1986)]. There is also known a process for the conversion of a 1-hydroxy-2-ketone compound into (S)-1,2-diol compound by using cells of a microorganism (cf. JP-A-1-320988). However, these processes are a process for the production of a 1,2-diol compound by utilizing an asymmetric reduction with an enzyme or a microorganism, which is clearly distinguished from the process of the present invention which comprises treating a racemic chlorohydrin compound with cells of a microorganism and thereby converting only one optically active chlorohydrin in a racemic mixture into a 1,2-diol compound.

Besides, for the purpose of producing an optically active 3-hydroxy-γ-butyrolactone which is useful as an intermediate for the production of optically active compound to be used as a medicament, there are known various chemical processes and also some biological processes, for example, a process for the production of an optically active 3-hydroxy-γ-butyrolactone or the corresponding ester by transesterification of a 3-hydroxy-γ-butyrolactone with a lipase (cf. EP 0439779); a process for the production of (R)-3-hydroxy-γ-butyrolactone by asymmetrically reducing ethyl 4-t-butoxy-3-oxobutyrate with a baker's yeast, and converting the resulting (R)-4-t-butoxy-3-hydroxybutyrate into the desired compound in the presence of fluoroacetic acid (cf. Synthesis (1), pp. 37–40, 1986). However, these processes have some problems to be solved, that is, they require complicated procedures or use of very expensive agents and further require very expensive or hardly available starting materials. Besides, they are limited to the production of only one optically active compound among two isomers. Accordingly, these processes are not satisfactory for producing an optically active 3-hydroxy-γ-butyrolactone with ease and low cost.

The present inventors had previously found a process for the production of an optically active compound from the corresponding racemic compound by using a microorganism which can hydrolyze and metabolize one of the optical isomers and hence can grow by utilizing the isomer as a single carbon source, for example, a process for the production of S-(+)-3-halogeno-1,2-propanediol using a bacteria of the genus *Alcaligenes* (cf. JP-A-3-191795, and J. of Fermentation & Bioengineering, Vol. 73, No. 6, pp. 443-448, 1992); a process for the production of R-(-)-3-halogeno-1, 2-propandiol using a bacteria of the genus *Pseudomonas* (cf. JP-A-3-191794, and Applied Microbiology and Biotechnology, Vol. 40, pp. 273-278, 1993); a process for the production of an optically active dichloropropanol (R isomer) by using a bacteria of the genus *Alcaligenes* (cf. JP-A-3-180197, and J. of Industrial Microbiology, Vol. 10, pp. 37-43, 1992); a process for the production of an optically active dichloropropanol (S isomer) by using a bacteria of the genus *Pseudomonas* (cf. JP-A-61-132196, and Agric. Biol. Chem., Vol. 54, No. 12, pp. 3185-3190, 1990); and a process for the production of an optically active epichlorohydrin by treating an optically active dichloropropanol with an alkali, wherein said optically active dichloropropanol is obtained by using a bacteria of the genus *Pseudomonas* (cf. JP-A-1-55879, and Bulletin. of Association of Synthetic Organic Chemistry, Vol. 51, No. 5, pp. 388-398, 1993).

BRIEF DESCRIPTION OF THE INVENTION

The present inventors have intensively studied to find an improved process for the production of an optically active chlorohydrin compound from a racemic chlorohydrin on an industrial scale, and have found that a certain microorganisms, particularly bacteria of the genuses *Pseudomonas*, *Enterobacter*, *Citrobacter* and *Bacillus* can degrade only one of the optical isomers of racemic mixture of chlorohydrin compound, or convert one of the isomers into an optically active 1,2-diol compound owing to a degrading activity thereof, and optionally can further convert into an optically active 3-hydroxy-γ-butyrolactone, and hence, there can be obtained optically active 1,2-diol compound and/or an optically active 3-hydroxy-γ-butyrolactone as well as an optically active chlorohydrin compound. According to the investigation of the present inventors, it has been found that since these microorganisms can not assimilate one of the starting racemic mixture, contrary to the above-mentioned processes for the production of optically active halogenopropanediol or dichloropropanol, and hence, it can not be used for the production of the optical isomer simultaneously with growing the microorganism in the medium. However, when the cells of the microorganism grown separately are applied to a racemic chlorohydrin compound, only one of the isomers is degraded, and another one of the isomers is remained in the reaction system, from which the desired optically active chlorohydrin compound can be recovered. It has also been found that, depending on the kinds of the microorganisms and/or on the kinds of the starting compounds, only one of the optical isomers can be converted into the corresponding 1,2-diol compound and/or 3-hydroxy-γ-butyrolactone, and hence, there can be obtained an optically active 1,2-diol compound and/or an optically active 3-hydroxy-γ-butyrolactone in addition to the optically active chlorohydrin compound.

Thus, an object of the invention is to provide a process for the production of an optically active chlorohydrin compound which comprises stereoselectively degrading one of the optical isomers in a cheap racemic mixture of chlorohydrin compound with a microorganism and recovering the remaining optically active chlorohydrin from the reaction mixture.

Another object of the invention is to provide a process for the production of an optically active 1,2-diol compound and/or an optically active 3-hydroxy-γ-butyrolactone in addition to the optically active chlorohydrin compound, which comprises treating a racemic mixture of chlorohydrin compound with a microorganism and thereby dechlorinating it to convert into an optically active 1,2-diol compound, and further to convert into an optically active 3-hydroxy-γ-butyrolactone, and then recovering these optically active compounds together with the remaining optically active chlorohydrin compound.

These and other objects and advantages of the present invention will be apparent to those skilled in the art from the following description.

DETAILED DESCRIPTION OF THE INVENTION

This invention provides a process for the production of an optically active chlorohydrin compound, which comprises treating a racemic mixture of a chlorohydrin compound of the formula:

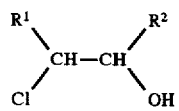

wherein $R^1$ is a hydrogen atom or a lower alkyl group; and $R^2$ is a substituted or unsubstituted lower alkyl group when $R^1$ is a hydrogen atom, provided that a hydroxymethyl group ($-CH_2OH$) is excluded, or $R^2$ is a hydrogen atom when $R^1$ is a lower alkyl group, with a microorganism, and thereby degrading selectively only one of the optical isomers in the racemic mixture, and then, recovering the another optically active isomer remained in the reaction system.

In the above process, depending on the kinds of the starting compounds and of the microorganisms, one of the optical isomers is converted to give an optically active 1,2-diol compound of the formula:

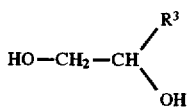

wherein $R^3$ is a substituted or unsubstituted lower alkyl group, and also an optically active 3-hydroxy-butyrolactone of the formula:

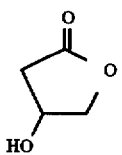

and hence, there are obtained an optically active 1,2-diol compound and/or an optically active 3-hydroxy-γ-butyrolactone in addition to the optically active chlorohydrin compound.

In the present description, the term "lower alkyl group" for $R^1$ denotes an alkyl group having 1 to 4 carbon atoms, such as methyl, ethyl, propyl, butyl. The term "lower alkyl group" in the "substituted or unsubstituted lower alkyl" for $R^2$ and $R^3$ denotes an alkyl group having 1 to 3 carbon atoms, such as methyl, ethyl, propyl, and the substituents for the alkyl group includes a cyano group, a lower alkoxycarbonyl group of the formula: $-COOR'$ ($R'$ is a straight chain or branched chain alkyl group having 1 to 4 carbon atoms, such as methyl, ethyl, propyl, isopropyl, butyl), or a lower alkoxy group of the formula: $-OR''$ ($R''$ is a straight chain or branched chain alkyl group having 1 to 4 carbon atoms, such as methyl, ethyl, propyl, isopropyl, butyl). Preferred examples of the substituted lower alkyl group are a cyanomethyl, a lower alkoxycarbonylmethyl, and a lower alkoxymethyl.

The microorganisms used in this invention include any microorganism which can selectively degrade one of the optical isomers of the racemic chlorohydrin compound of the formula [1], preferably bacteria of the genuses *Pseudomonas, Enterobacter, Citrobacter* and *Bacillus*. Among them, particularly preferred ones are *Pseudomonas* sp. OS-K-29, *Pseudomonas* sp. DS-K-NR 818, *Enterobacter* sp. DS-S-75, *Citrobacter freundii* DS-S-13, *Citrobacter freundii* DS-K-40, and *Bacillus sphaericus* DS-ID-819. These microorganisms have no ability of assimilating the chlorohydrin compound [1], and hence, the cells obtained by growing them are used for the stereoselective degradation of the racemic chlorohydrin compound.

Thus, the preferred embodiment of the present invention is a process as shown in the following Reaction Scheme-1 (provided that only when the $R^3$ in the formula [1a] is a lower alkoxycarbonylmethyl, the 3-hydroxy-γ-butyrolactone [3a] is produced):

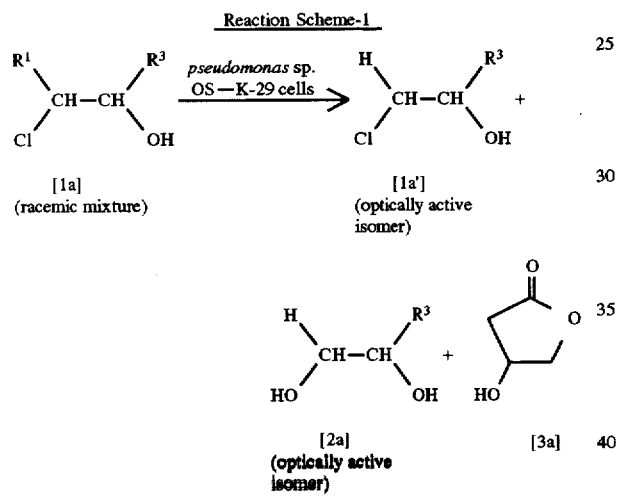

wherein $R^3$ is the same as defined above.

In the process as shown in the above Reaction Scheme-1, more preferred embodiment is a process using a compound of the formula [1a] wherein $R^3$ is a cyanomethyl or a lower alkoxycarbonylmethyl.

In the process of the above Reaction Scheme-1 wherein $R^3$ is a lower alkoxycarbonylmethyl, there are produced an optically active 3-hydroxy-γ-butyrolactone [3a] in addition to the optically active 1,2-diol compound [2a], and these optically active 1,2-diol compound [2a] and optically active 3-hydroxy-γ-butyrolactone [3a] are usually in the form of R-isomer as shown by the following formula, respectively.

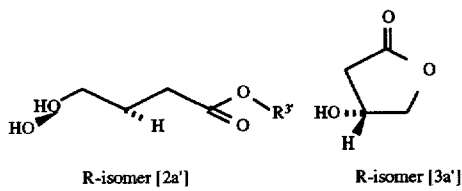

wherein $R^{3'}$ is a lower alkoxycarbonylmethyl group.

Another preferred embodiment of the present invention is a process as shown by the following Reaction Scheme-2:

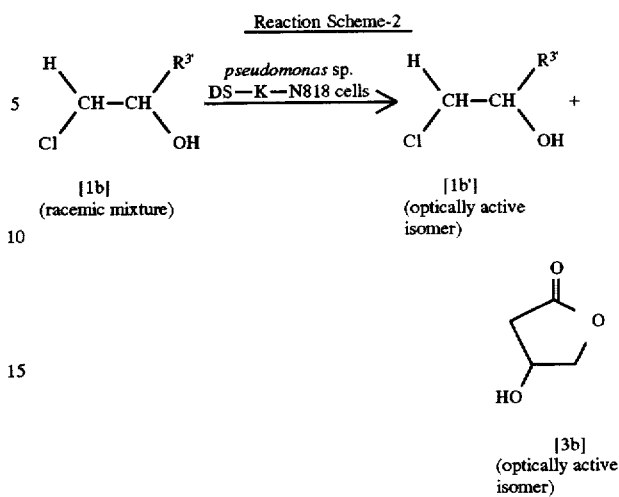

wherein $R^{3'}$ is the same as defined above.

In the process of the above Reaction Scheme-2, other bacteria of the genus Enterobacter, Citrobacter and Bacillus as mentioned hereinbefore are also preferably used.

The optically active 3-hydroxy-γ-butyrolactone [3b] obtained by this process is usually in the form of an S-isomer as shown by the following formula, while in case of using *Bacillus sphaericus* DS-ID-819 and using the starting compound [1 b] wherein $R^{3'}$ is other than n-butyloxy carbonylmethyl group, the product is in the form of an R-isomer.

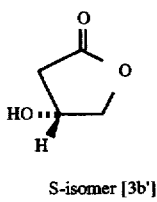

S-isomer [3b']

A further preferred embodiment of the present invention is a process as shown by the following Reaction Scheme-3:

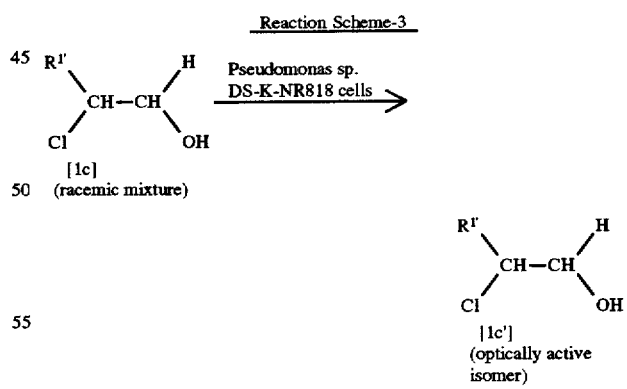

wherein $R^{1'}$ is a lower alkyl group.

The specific microorganism, Pseudomonas sp. OS-K-29 used in the present invention has been isolated from a soil by the present inventors, and Pseudomonas DS-K-NR 818 is a mutant thereof. These microorganisms have been classified in accordance with Bergey's Manual of Systematic Bacteriology, 8th and 9th Editions based on the morphological and physiological properties of them. As a result, they are Gram negative, aerobic rods and have polar flagella and are positive in the test with an oxidase and a catalase, and hence, they have been identified as a species of the genus Pseudomonas, and further since they are not identical to any known species, they have been designated as mentioned above and have been deposited to National Institute of Bioscience and Human-Technology, Agency of Industrial Science and Technology, Japan under Budapest Treaty with an accession number of FERM BP-994 and FERM BP-5491, respectively.

The mycological properties of Pseudomonas sp. OS-K-29 are disclosed in JP-A-1-55879.

The *Pseudomonas* OS-K-29 can be cultured in any conventional medium in which this microorganism can grow. The medium contains, for example, a carbon source such as hydrocarbons (e.g. glucose, galactose, sucrose), alcohols (e.g. glycerol, racemic 3-halogeno-1,2-propandiol, (R)- or (S)-3-halogeno-1,2-propandiol, racemic 2,3-dichloro-1-propanol, (R)-2,3-dichloro-1-propanol), organic acids (e.g. acetic acid, citric acid, malic acid, maleic acid, fumaric acid, gluconic acid) or salts thereof, or a mixture thereof; a nitrogen source such as inorganic nitrogen compounds (e.g. ammonium sulfate, ammonium nitrate, ammonium phosphate), organic nitrogen compounds (e.g. urea, peptone, casein, yeast extract, meat extract, corn steep liquor), or a mixture thereof; and may further contain an inorganic salt (e.g. a phosphate, a magnesium salt, a potassium salt, a manganese salt, an iron salt, a zinc salt, a copper salt) and further vitamins. In order to obtain cells of these microorganisms having high enzymatic activities, the medium as mentioned above and a nutrient medium such as a peptone medium, a bouillon medium for culturing of the microorganism may further include a racemic 3-halogeno-1,2-propanediol, (R)- or (S)-3-halogeno-1,2-propanediol, a racemic 2,3-dichloro-1-propanol, and (R)-2,3-dichloro-1-propanol. It may also be effective to use a completely synthetic medium containing as a single carbon source a racemic 2,3-dichloro-1-propanol, (R)-2,3-dichloro-1-propanol, or a racemic 3-halogeno-1,2-propanediol. The culture of the above micro-organisms can be carried out in a usual manner, for example, at a pH 6–9, preferably pH 6.5–7.5, a temperature of 20° to 40° C., preferably 25 to 37° C., under an aerobic condition, for 10 to 96 hours.

The mycological properties of Pseudomonas sp. DS-K-NR 818 are as follows:

A. Morphological properties
 Shape of cells: rods
 Size of cells: 0.4–0.6×1.2–1.6 μm
 Pleomorphisms of cells: none
 Mobility: +, polar flagella
 Spores: none
 Gram stain: negative
 Acid fastness: none
B. Growth in various media
 1. Bouillon-agar medium (culture at 30° C. for 3 days)
  1) Speed of colony growth: ordinary
  2) Shape of colonies: circular
  3) Shape of colony surface: smooth
  4) Raised condition of colonies: convex
  5) Periphery of colonies: entire
  6) Contents of colonies: homogeneous
  7) Color of colonies: milky white
  8) Gloss of colonies: dull
  9) Transparency of colonies: translucent
  10) Formation of soluble pigment: none 2. Bouillon-agar slant medium (culture at 30° C. for 3 days)
  1) Growth degree: good
  2) Growth condition: filiform
  3) Shape of colony surface: smooth
  4) Shape of colonies in section: flat
  5) Gloss of colonies: dull
  6) Color of colonies: milky white
  7) Transparency of colonies: translucent
 3. Bouillon liquid stationary culture (at 30° C. for 3 days)
  1) Growth condition: somewhat turbid
  2) Generation of gas: none
  3) Coloring of medium: none
  4) Liquification of gelatin: no liquification
  5) Litmus milk: no agglutination, no change
C. Physiological properties
 Decarboxylation of lysine: positive
 VP test: negative
 MR test negative
 Reduction of nitrate: negative
 Production of indole: negative
 PPA reaction: negative
 Production of hydrogen sulfide: negative
 Utilization of citric acid: positive
 Hydrolysis of starch: negative
 Denitrification: negative
 Utilization of inorganic salts: positive
 Production of pigment:
  1) King's A medium: negative
  2) King's B medium: negative
  3) *Pseudomonas* P medium: negative
  4) *Pseudomonas* F medium: negative
 Catalase: positive
 Oxidase: positive
 Urease test: positive
 OF-test (by Hugh Leifson method, no gas generation):
  1) D-Glucose: negative
  2) Glycerin: oxidative
  3) D-Galactose: negative
  4) D-Fructose: negative
  5) D-Trehalose: negative
 Accumulation of PHB: positive
 Utilization of carbon source:
  1) D-Mannitol: negative
  2) D-Fructose: positive
  3) D-Glucose: negative
  4) D-Gluconic acid: positive
  5) D-Galactose: negative
  6) Glycerin: positive
  7) p-Hydroxybenzoic acid: positive
 Optimum pH for growth: 5–9
 Optimum temperature for growth: 20°–40° C.

The *Pseudomonas* DS-K-NR 818 can be cultured in any conventional medium in which this microorganism can grow. The medium contains, for example, a carbon source such as hydrocarbons (e.g. fructose), alcohols (e.g. glycerol, racemic 3-halogeno-1,2-propandiol, racemic 2,3-dichloro-1-propanol), organic acids (e.g. acetic acid, citric acid, malic acid, maleic acid, fumaric acid, gluconic acid) or salts thereof, or a mixture thereof; a nitrogen source such as inorganic nitrogen compounds (e.g. ammonium sulfate, ammonium nitrate, ammonium phosphate), organic nitrogen compounds (e.g. urea, peptone, casein, yeast extract, meat extract, corn steep liquor), or a mixture thereof; and may further contain an inorganic salt (e.g. a phosphate, a magnesium salt, a potassium salt, a manganese salt, an iron salt, a zinc salt, a copper salt) and further vitamins. In order to obtain cells of these microorganisms having high enzymatic activities, the medium as mentioned above and a nutrient medium such as a peptone medium, a bouillon medium for culturing of the microorganism may further include a racemic 3-halogeno-1,2-propanediol, 2,3-dichloro-1-propanol. It may also be effective to use a completely synthetic medium containing as a single carbon source a racemic 3-halogeno-1,2-propanediol or 2,3-dichloro-1-propanol. The culture of the above microorganism can be carried out in a usual manner, for example, at a pH 6–9, preferably pH 6.5–7.5, a temperature of 20° to 40° C., preferably 25° to 37° C., under an aerobic condition, for 10 to 96 hours.

The other microorganisms used in the present invention, Enterobacter sp. DS-S-75, *Citrobacter freundii* DS-S-13, *Citrobacter freundii* DS-K-40, and *Bacillus sphaericus* DS-ID-819 have also been isolated from a soil by the present inventors. These microorganisms have been classified in accordance with Bergey's Manual of Systematic Bacteriology, 9th Edition based on the morphological and physiological properties of them. As a result, the *Enterobacter sp.* DS-S-75 is Gram negative, facultative anaerobic rods and has peripheral flagella and is positive in V-P test, negative in MR test and negative in DNase activity, and hence, it has been identified as a species of the genus *Enterobacter*, and further since it is not identical to any known species, it has been designated as mentioned above and has been deposited to National Institute of Bioscience and Human-Technology, Agency of Industrial Science and Technology, Japan under Budapest Treaty with an accession number of FERM BP-5494. Likewise, the *Citrobacter freundii* DS-S-13 and *Citrobacter freundii* DS-K-40 are Gram negative, facultative anaerobic rods and have peripheral flagella and are negative in V-P test and can utilize citric acid as a single carbon source, and hence, they have been identified as a species of the genus Citrobacter. According to a further test, they produce hydrogen sulfide. In view of these properties., they are identified as a strain of *Citrobacter freundii* and have been designated as mentioned above and have been deposited to National Institute of Bioscience and Human-Technology, Agency of Industrial Science and Technology, Japan under Budapest Treaty with an accession number of FERM BP-5492 and FERM BP-5493, respectively. Likewise, the *Bacillus sphaericus* DS-ID-819 is Gram positive, aerobic rods, has peripheral flagella, forms spores, and is positive in catalase test, and hence, it has been identified as a species of the genus bacillus. In view of the physiological properties in addition to those properties, it has been designated as a strain of *Bacillus sphaericus* and has been deposited to National Institute of Bioscience and Human-Technology, Agency of Industrial Science and Technology, Japan under Budapest Treaty with an accession number of FERM BP-5495.

The mycological properties of Enterobacter sp. DS-S-75 are as follows:

A. Morphological properties
   Shape of cells: rods
   Size of cells: 0.6–0.8.33 1.5–2.8 μm
   Pleomorphisms of cells: none
   Mobility: +, peripheral flagella
   Spores: none
   Gram stain: negative B. Growth in various media
   1. Bouillon-agar medium (culture at 30° C. for 3 days)
      1) Size of colonies: 3–4 mm
      2) Shape of colonies: irregular
      3) Speed of colony growth: rapidly
      4) Shape of colony surface: smooth, mucoid
      5) Raised condition of colonies: convex
      6) Periphery of colonies: undulate
      7) Color of colonies: milky white
      8) Gloss of colonies: dull
      9) Transparency of colonies: opaque
      10) Formation of soluble pigment: none
   2. Bouillon-agar slant medium (culture at 30° C. for 3 days)
      1) Growth degree: good
      2) Growth condition: filiform
      3) Gloss of colonies: dull
      4) Color of colonies: milky white
   3. Bouillon liquid stationary culture (at 30° C. for 3 days)
      1) Growth condition: turbid
      2) Coloring of medium: none
      3) Sediment: observed C. Physiological properties
   Production of indole: negative
   Catalase: positive
   Urease: positive
   Oxidase: negative
   β-Galactosidase: positive
   Lysine decarboxylase: positive
   Production of hydrogen sulfide: negative
   Utilization of citric acid: positive
   Hydrolysis of starch: negative
   Liquification of gelatin: negative
   MR test: negative
   VP test: positive
   Reduction of nitrate: positive
   Denitrification: positive
   DNase activity: negative
   NPTase: positive
   O-F test (glucose): fermentative
   D-Glucose, acid: positive
   D-Glucose, gas: positive
   Decomposition of saccharides (production of acid in +)
   D-Mannitol: +
   Sucrose: +
   Lactose:
   D-Sorbitol: +
   Utilization of carbon source:
   D-Glucose: positive
   D-Galactose: positive
   Lactose: positive
   Sucrose: positive
   D-Mannitol: positive
   Glycerin: positive
   D-Gluconic acid: positive
   p-Hydroxybenzoic acid: positive
   D-Galactitol: positive
   D-Sorbitol: positive Optimum temperature for growth: 30°–37° C.
Optimum pH for growth: 5–9
The mycological properties of *Citrobacter freundii* DS-S-13 are as follows:
A. Morphological properties
 Shape of cells: rods
 Size of cells: 0.5–0.7×1.8–3.6 μm
 Pleomorphisms of cells: none
 Mobility: +, peripheral flagella
 Spores: none
 Gram stain: negative
B. Growth in various media
 1. Bouillon-agar medium (culture at .30° C. for 3 days)
  1) Size of colonies: 2–4 mm
  2) Shape of colonies: circular
  3) Speed of colony growth: rapidly
  4) Shape of colony surface: smooth
  5) Raised condition of colonies: convex
  6) Periphery of colonies: entire
  7) Color of colonies: milky white
  8) Gloss of colonies: shiny surface
  9) Transparency of colonies: translucent
  10) Formation of soluble pigment: none
 2. Bouillon-agar slant medium (culture at 30° C. for 3 days)
  1) Growth degree: good
  2) Growth condition: echinulate
  3) Gloss of colonies: shiny surface
  4) Color of colonies: milky white
 3. Bouillon liquid stationary culture (at 30° C. for 3 days)
  1) Growth condition: turbid
  2) Coloring of medium: none
  3) Sediment: observed
C. Physiological properties
 Production of indole: negative
 Catalase: positive
 Urease: positive
 Oxidase: negative
 β-Galactosidase: positive
 Lysine decarboxylase: negative
 Production of hydrogen sulfide: positive
 Utilization of citric acid: positive
 Hydrolysis of starch: negative
 Liquification of gelatin: negative
 MR test: positive
 VP test: negative
 Reduction of nitrate: positive
 Denitrification: positive
 DNase activity: negative
 NPTase: negative
 O-F test (glucose): fermentative
 D-Glucose, acid: positive
 D-Glucose, gas: positive
 Decomposition of saccharides (production of acid in +)
 D-Mannitol: +
 Sucrose: +
 Lactose: +
 D-Sorbitol: +
 Utilization of carbon source:
 D-Glucose: positive
 D-Galactose: positive
 Lactose: positive
 Sucrose: positive
 D-Mannitol: positive
 Glycerin: positive
 D-Gluconic acid: positive
 p-Hydroxybenzoic acid: positive
 D-Galactitol: negative
 D-Sorbitol: positive
Optimum temperature for growth: 25°–30° C.
Optimum pH for growth: 5–9
The mycological properties of *Citrobacter freundii* DS-K-40 are as follows:
A. Morphological properties
 Shape of cells: rods
 Size of cells: 0.5–0.7×1.8–3.6 μm
 Pleomorphisms of cells: none
 Mobility: +, peripheral flagella
 Spores: none
 Gram stain: negative
B. Growth in various media
 1. Bouillon-agar medium (culture at 30° C. for 3 days)
  1) Size of colonies: 2–4 mm
  2) Shape of colonies: circular
  3) Speed of colony growth: rapidly
  4) Shape of colony surface: smooth
  5) Raised condition of colonies: convex
  6) Periphery of colonies: entire
  7) Color of colonies: milky white
  8) Gloss of colonies: shiny surface
  9) Transparency of colonies: translucent
  10) Formation of soluble pigment: none
 2. Bouillon-agar slant medium (culture at 30° C. for 3 days)
  1) Growth degree: good
  2) Growth condition: echinulate
  3) Gloss of colonies: shiny surface
  4) Color of colonies: milky white
 3. Bouillon liquid stationary culture (at 30° C. for 3 days)
  1) Growth condition: turbid
  2) Coloring of medium: none
  3) Sediment: observed
C. Physiological properties
 Production of indole: negative
 Catalase: positive
 Urease: positive
 Oxidase: negative
 β-Galactosidase: positive
 Lysine decarboxylase: negative
 Production of hydrogen sulfide: positive
 Utilization of citric acid: positive
 Hydrolysis of starch: negative
 Liquification of gelatin: negative
 MR test: positive
 VP test: negative
 Reduction of nitrate: positive
 Denitrification: positive
 DNase activity: negative
 NPTase: negative
 O-F test (glucose): fermentative D-Glucose, acid: positive
D-Glucose, gas: positive
Decomposition of saccharides (production of acid in +)
D-Mannitol: +
Sucrose: +
Lactose: +
D-Sorbitol: +
Utilization of carbon source:
D-Glucose: positive
D-Galactose: positive
Lactose: positive
Sucrose: positive
D-Mannitol: positive
Glycerin: positive
D-Gluconic acid: positive
p-Hydroxybenzoic acid: positive
D-Galactitol: negative
D-Sorbitol: positive
Optimum temperature for growth: 25°–300° C.
Optimum pH for growth: 5–9

The mycological properties of Bacillus sphaericus DS-ID-819 are as follows:

A. Morphological properties
Shape of cells: rods
Size of cells: 0.5–0.7×2.0–3.5 µm
Pleomorphisms of cells: none
Mobility: +, peripheral flagella
Spores: endospore
Gram stain: positive B. Growth in various media
  1. Bouillon-agar medium (culture at 300° C. for 3 days)
    1) Size of colonies: 2–4 mm
    2) Shape of colonies: circular
    3) Speed of colony growth: ordinary
    4) Shape of colony surface: wrinkled
    5) Raised condition of colonies: flat
    6) Periphery of colonies: entire
    7) Color of colonies: milky white
    8) Gloss of colonies: dull
    9) Transparency of colonies: translucent
    10) Formation of soluble pigment: none
  2. Bouillon-agar slant medium (culture at 30° C. for 3 days)
    1) Growth degree: good
    2) Growth condition: spreading
    3) Gloss of colonies: dull
    4) Color of colonies: milky white
  3. Bouillon liquid stationary culture (at 30° C. for 3 days)
    1) Growth condition: somewhat turbid
    2) Coloring of medium: none
    3) Sediment: none C. Physiological properties
Production of indole: negative
Catalase: positive
Urease: positive
Oxidase: positive
β-Galactosidase: negative
Lysine decarboxylase: positive
Production of hydrogen sulfide: negative
Utilization of citric acid: positive
Hydrolysis of starch: negative
Liquification of gelatin: positive
MR test: negative
VP test: negative
Reduction of nitrate: negative
Denitrification: negative
DNase activity: positive
NPTase: negative
O-F test (glucose): oxidative
D-Glucose, acid: negative
D-Glucose, gas: negative
Decomposition of saccharides (production of acid in +)
D-Mannitol:
Sucrose:
Lactose:
D-Sorbitol:
Utilization of carbon source:
D-Glucose: negative
D-Galactose: negative
Lactose: negative
Sucrose: negative
D-Mannitol: negative
Glycerin: positive
D-Gluconic acid: negative
Sodium acetate: positive
Glycine: positive
D-Galactitol: negative
D-Sorbitol: negative
Optimum temperature for growth: 30°–37° C.
Optimum pH for growth: 6–9

The above microorganisms, Enterobacter sp. DS-S-75, Citrobacter freundii DS-S-13, Citrobacter freundii DS-K-40, and Bacillus sphaericus DS-ID-819 can be cultured in any conventional medium in which these microorganisms can grow. The medium contains, for example, a carbon source such as hydrocarbons (e.g. glucose, galactose, fructose), alcohols (e.g. glycerol), organic acids (e.g. acetic acid, citric acid, malic acid, maleic acid, fumaric acid, gluconic acid) or salts thereof, or a mixture thereof; a nitrogen source such as inorganic nitrogen compounds (e.g. ammonium sulfate, ammonium nitrate, ammonium phosphate), organic nitrogen compounds (e.g. urea, peptone, casein, yeast extract, meat extract, corn steep liquor), or a mixture thereof; and may further contain an inorganic salt (e.g. a phosphate, a magnesium salt, a potassium salt, a manganese salt, an iron salt, a zinc salt, a copper salt) and further vitamins. The culture of the above microorganisms can be carried out in a usual manner, for example, at a pH 5–9, preferably pH 6.5–7.0, a temperature of 20° to 40° C., preferably 25° to 37° C., under an aerobic condition, for 10 to 96 hours.

The production of an optically active chlorohydrin and an optically active 1,2-diol compound and/or an optically active 3-hydroxy-γ-butyrolactone by the treatment of a racemic chlorohydrin compound with a microorganism may be carried out by using the microorganism in the form of 1) a culture broth obtained by culturing the microorganism in the method as described above, 2) cells of the microorganism obtained by centrifuge of the culture broth or a processed product of the cells (e.g. fractured cells or cell extracts), or 3) an immobilized product of these cells or processed products thereof. The biological optical resolution of this invention is carried out by using these microbial cell products. The microbial cell product is mixed in a buffer, and the substrate (i.e. racemic chlorohydrin compound) is added to said mixture of microbial cell product in a buffer and then is subjected to the degradation reaction. The reaction is preferably carried out at a temperature of 15° to 50° C. and at a pH 6 to 9. The substrate is preferably contained in a concentration of 0.1 to 15 %(v/v). The substrate may be added in one time at the beginning of the reaction or may be added dividedly. The reaction is usually carried out with stirring or shaking, and the reaction period of time may vary depending on the concentration of the substrate and the amount of microbial cell product, but is usually in the range of 1 to 120 hours. Preferably, the endpoint of the reaction is determined by analysis with gas chromatography etc., that is, when the resulting optically active product reaches to the maximal optical purity.

The optically active chlorohydrin and an optically active 1,2-diol compound and/or an optically active 3-hydroxy-γ-butyrolactone contained in the reaction mixture are collected and purified by a conventional method. For instance, after removing the microbial cell product by centrifuge, the supernatant is concentrated with an evaporator, and extracted with a solvent (e.g. ethyl acetate). The extract is dried over anhydrous magnesium sulfate and the solvent is evaporated under reduced pressure to give a syrup of the optically active chlorohydrin compound. When an optically active 1,2-diol compound is produced, the syrup contains also the 1,2-diol compound together with the optically active chlorohydrin compound, and hence, these compounds are separated and purified by distillation or column chromatography. Besides, when an optically active 3-hydroxy-γ-butyrolactone is produced, it is also isolated in the following manner. That is, the reaction mixture is centrifuged to remove the microbial cell product, and the supernatant is extracted with a solvent (e.g. ethyl acetate), and the optically active chlorohydrin and 1,2-diol compounds are separated, and the remaining aqueous layer is concentrated to give a crude syrup of the optically active 3-hydroxy-γ-butyrolactone. Alternatively, the aqueous layer may be treated with an active carbon and then the desired compound is separated and purified in a usual manner. The products may further be purified by a conventional purification method such as treatment with an active carbon, or a silica gel column chromatography.

The present invention is illustrated in more detail by the following Examples but should not be constructed to be limited thereto. Unless otherwise indication, percentages in the examples are expressed by w/v percentage.

EXAMPLE 1

2.5 L of a nutrient medium (pH 7.2) containing each 1% of peptone, yeast extract and glycerol were added into a 5 L volume jar fermentar and steriled at 121° C. for 15 minutes under high pressure. *Pseudomonas* sp. OS-K-29 strain was previously subjected to a shake culture at 30° C. for 16 hours in a nutrient medium (pH 7.2) containing each 1.0% of peptone, yeast extract and glycerol to give a seed culture, and the seed culture thus obtained was inoculated on the above medium in an amount of 2% (v/v) under sterile condition. Then, the inoculated medium was subjected to an agitation culture under aeration of 1.0 L/min at 30° C. for about 24 hours at 500 rpm. After completion of the cultivation, the culture solution was centrifuged to collect the cells and the cells were washed with 20 mM phosphate buffer solution (pH 7.2, containing 2 mM magnesium sulphate) three times to give resting cells. The cells were suspended in 100 ml of the same buffer solution containing 1.0% calcium carbonate in a 500 ml volume Erlenmeyer flask with baffle and added thereto 1.0% (v/v) of racemic 4-chloro-3-hydroxybutyronitrile and then they were reacted at 30° C. for 90 hours with stirring. The reaction mixture was subjected to a gas chromatography (column support material: PEG 20M, 60–80 mesh) for determination of remaining 4-chloro-3-hydroxybutyronitrile. The percentage of remaining 4-chloro-3-hydroxybutyronitrile was 40.1%. After completion of the reaction, the reaction mixture was centrifuged to remove the cells, concentrated to about 1 ml and extracted with ethyl acetate. After dehydration with anhydrous magnesium sulphate, the solvent was removed in vacuo to give 380 mg of 4-chloro-3-hydroxybutyronitrile and 350 mg of 1,2-diol compound which corresponded to the substrate. The identification and determination of this material were carried out by the gas chromatography as described above and confirmed by its retention time.

This syrup was subjected to a gas chromatography using a capillary column G-TA (0.25 mm×30 m, manufactured by Advanced Separation Technologies Inc., NJ, USA) to analyse optical isomers of 4-chloro-3-hydroxybutyronitrile therein. Separately, 1,2-diol compound was analyzed by the above gas chromatography as to the optical isomers likewise, after being trifluorated with anhydrous trifluoroacetic acid. It was shown by the results that the recovered 4-chloro-3-hydroxybutyronitrile was S-isomer of optical purity 94.5%ee. It was also shown that the recovered 1,2-diol compound was R-isomer of optical purity 42.2%ee. The above gas chromatography analysis for optical isomers was carried out under the following conditions. The retention time of 4-chloro-3-hydroxybutyronitrile was 64.1 min (S-isomer) and 66.5 min (R-isomer). The retention time of 1,2-diol compound was 113.1 min (S-isomer) and 125.3 min (R-isomer).

Conditions for analysis:

Column temperature: 120° C.; detector temperature: 200° C.; carrier gas: nitrogen; flow rate: 0.5 ml/min; detector: FID; split ratio: 100/1.

EXAMPLES 2 TO 7

The reaction was carried out by the same procedure as in Example 1 except that substrates shown in Table 1 were substituted for racemic 4-chloro-3-hydroxybutyronitrile. The identification and determination as well as analysis for optical isomers of the various compounds thus obtained were carried out by the same procedure as in Example 1.

In Examples 3 to 5, 3-hydroxy-γ-butyrolactone was obtained as a crude syrup by removing the cells from the reaction mixture, treating the supernatant with the same amount of ethyl acetate to extract chlorohydrin and 1,2-diol compound and concentrating the aqueous layer. This material was identified and determined by the gas chromatography as described in Example 1 and confirmed by its retention time. The optical purity of 3-hydroxy-γ-butyrolactone in this syrup was determined by the gas chromatography using a capillary column G-TA (0.25 mm×30 m, manufactured by Advanced Separation Technologies Inc., NJ, USA) as described in Example 1, after being acetylated with acetyl chloride. The retention time of 3-hydroxy-γ-butyrolactone was 11.3 min (S-isomer) and 12.0 min (R-isomer).

Conditions for analysis:

Column temperature: 150° C.; detector temperature: 200° C.; carrier gas: nitrogen; flow rate: 0.7 ml/min; detector: FID; split ratio: 100/1. The physical properties of the obtained 3-hydroxy-γ-lactone were well identical to the data described in "Synthetic Communications", 16(2), pp.183–190,1986.

¹H-NMR (CDCl₃, 250 MHz), δppm: 2.54 (d, 1 H, J=18 Hz); 2.79 (dd, 1 H, J=18 Hz;
J=6 Hz); 3.29 (s, 1 H, OH); 4.34 (d, 1 H, J=10 Hz); 4.46 (dd, 1 H, J=10 Hz,
J=4.5 Hz); 4.6–4.7 (m, 1 H);
¹³C-NMR (CDCl₃), δppm: 177, 76.3, 67.2, 37.7.

The products and their yield in Examples 1 to 7 are shown in Table 1.

TABLE 1

| Example | Substrate | Product (optical purity and yield) halohydrin |
|---|---|---|
| 1 | 4-Chloro-3-hydroxybutyronitrile | 94.5% ee(S), 381 mg |
| 2 | Methyl 4-chloro-3-hydroxybutyrate | 50.1% ee(S), 403 mg |
| 3 | Ethyl 4-chloro-3-hydroxybutyrate | 98.2% ee(S), 303 mg |
| 4 | Isopropyl 4-chloro-3-hydroxybutyrate | 98.3% ee(S), 310 mg |
| 5 | 1-Chloro-2-hydroxybutane | 95.6% ee(R), 341 mg |
| 6 | 1-Chloro-2-hydroxymethoxypropane | 75.3% ee(R), 350 mg |
| 7 | 1-Chloro-2-hydroxyethoxypropane | 56.3% ee(R), 351 mg |

| | Product (optical purity arid yield) | |
|---|---|---|
| Example | 1,2-diol | 3-hydroxy-γ-butyrolactone |
| 1 | 42.2% ee(R), 350 mg | |
| 2 | 49.1% ee(R), 280 mg | 48.2% ee(R), 111 mg |
| 3 | 41.1% ee(R), 210 mg | 39.2% ee(R), 70 mg |
| 4 | 42.3% ee(R), 220 mg | 40.7% ee(R), 80 mg |
| 5 | 78.6% ee(S), 401 mg | |
| 6 | 70.1% ee(S), 322 mg | |
| 7 | 51.4% ee(S), 326 mg | |

EXAMPLE 8

2.5 L of a nutrient medium (pH 7.0) containing each 1% of peptone, yeast extract and glycerol were added into of a 5 L volume jar fermentar and steriled at 121° C. for 15 minutes under high pressure. *Pseudomonas sp. DS-K-NR81 8* strain was previously subjected to a shake culture at 30° C. for 18 hours in a nutrient medium (pH 7.0) containing each 1.0% of peptone, yeast extract and glycerol to give a seed culture, and the seed culture was inoculated on the above medium in an amount of 2.0% (v/v) under sterile condition. Then, the inoculated medium was subjected to an seed culture under aeration of 0.5 L/min at 30° C. for about 24 hours with rotary mixing at 500 rpm. After completion of the cultivation, the culture solution was centrifuged to collect cells and the cells were washed with 20 mM phosphate buffer solution (pH 7.2, containing 2 mM magnesium sulphate) three times to give resting cells. The cells were suspended in 100 ml of the same buffer solution in a 500 ml volume Erlenmeyer flask with baffle and added thereto 1.0% (v/v) of racemic ethyl 4-chloro-3-hydroxybutyrate and they were reacted at 30° C. for 40 hours. The reaction mixture was subjected to a gas chromatography (column support material: PEG 20M, 60–80 mesh) for determination of remaining ethyl 4-chloro-3-hydroxybutyrate. The percentage of remaining ethyl 4-chloro-3-hydroxybutyrate was 41.8%. After completion of the reaction, the reaction mixture was centrifuged to remove the cells, concentrated to about 1 ml and extracted with ethyl acetate. After dehydration with anhydrous magnesium sulphate, the solvent was removed in vacuo to give 406 mg of ethyl 4-chloro-3-hydroxybutyrate. This material was identified and determined by the gas chromatography as described above and confirmed by its retention time.

Optical isomer of the remaining ethyl 4-chloro-3-hydroxybutyrate was analyzed by a gas chromatography using a capillary column G-TA (0.25 mm×30 m, manufactured by Advanced Separation Technologies Inc., NJ, USA).

It was shown by the results that the recovered ethyl 4-chloro-3-hydroxybutyrate was R-isomer of optical purity >98%ee. The above gas chromatography analysis for optical isomers was carried out under the following conditions. The retention time of ethyl 4-chloro-3-hydroxybutyrate was 39.5 min (R-isomer) and 41.0 min (S-isomer).

Conditions for analysis:

Column temperature: 110° C.; detector temperature: 200° C.; carrier gas: nitrogen; flow rate: 0.7 ml/min; detector: FID; split ratio: 100/1.

3-Hydroxy-γ-butyrolactone was obtained as a crude syrup by removing the cells from the reaction mixture treating the supernatant with a same amount of ethyl acetate to extract chlorohydrin and then concentrating the aqueous layer. The identification and determination as well as analysis for optical isomers of the compound were carried out by the same procedure as in Example 3.

EXAMPLES 9 TO 12

The reaction was carried out by the same procedure as in Example 8 except that substrates shown in Table 2 was substituted for racemic ethyl 4-chloro-3-hydroxybutyrate. The identification and determination as well as analysis for optical isomers of the various compounds thus obtained were also carried out by the same procedure as in Example 8.

The products and their yield in Examples 8 to 12 are shown in Table 2.

TABLE 2

| Example | Substrate |
|---|---|
| 8 | Ethyl 4-chloro-3-hydroxybutyrate |
| 9 | Methyl 4-chloro-3-hydroxybutyrate |
| 10 | Isopropyl 4-chloro-3-hydroxybutyrate |
| 11 | 2-Chloro-1-hydroxypropane |
| 12 | 2-Chloro-1-hydroxybutane |

| | Product (optical purity and yield) | |
|---|---|---|
| Example | chlorohydrin | 3-hydroxy-γ-butyrolactone |
| 8 | 98.3% ee(R), 406 mg | 62.5% ee(S), 360 mg |
| 9 | 97.2% ee(R), 264 mg | 35.6% ee(S), 235 mg |
| 10 | 95.9% ee(S), 424 mg | 72.4% ee(S), 380 mg |
| 11 | >98% ee(S), 441 mg | |
| 12 | >98% ee(S), 436 mg | |

EXAMPLE 13

Preparation of (S)-3-hydroxy-γ-butyrolactone and (R)-methyl 4-hydroxybutyrate 100 ml of a nutrient medium (pH 7.0) containing each 1% of peptone, yeast extract and glycerol were added into a 500 ml volume Erlenmeyer flask and steriled at 121 ° C. for 15 minutes under high pressure. *Enterobacter sp. DS-S-75* strain was previously subjected to a shake culture at 30° C. or 20 hours in a nutrient medium (pH 7.0) containing each 1.0% of peptone, yeast extract and glycerol to give a seed culture, and the seed culture was inoculated on the above medium in an amount of 2.0% (v/v) under sterile condition. Then, the inoculated medium was subjected to an agitation culture at 30° C. for about 24 hours. After completion of the cultivation, the culture solution was centrifuged to collect cells and the cells were washed with 20 mM phosphate buffer solution (pH 7.2, containing 2 mM magnesium sulphate) three times to give resting cells. The cells were suspended in 100 ml of the same buffer solution in a 500 ml Erlenmeyer flask with baffle and added thereto 1.0% (v/v) of racemic methyl 4-chloro-3-hydroxybutyrate, and they were reacted at 30° C. for 24 hours. The reaction mixture was subjected to a gas chromatography (column support material: PEG 20M, 60–80 mesh) for determination of remaining methyl 4-chloro-3-hydroxybutyrate. The percentage of remaining methyl 4-chloro-3-hydroxybutyrate was 48.0%. After completion of the reaction, the reaction mixture was centrifuged to remove the cells and the supernatant was flowed through a column packed with active carbon and eluted with acetone. Acetone was evaporated in vacuo from eluate, and the residual oily substance was distilled to give 342 mg of (R)-methyl 4-chloro-3-hydroxybutyrate (b.p. 75–80/1.5 mmHg) and 214 mg of (S)- 3-hydroxy-γ-butyrolactone (b.p. 110–120/0.5 mmHg) as an oil.

The obtained methyl 4-chloro-3-hydroxybutyrate was R-isomer of optical purity >99%ee. The obtained 3-hydroxy-γ-butyrolactone was acetylated with acetyl chloride and then determined its optical purity. Said 3-hydroxy-γ-butyrolactone was S-isomer of optical purity 95.9%ee.

A gas chromatography using a capillary column G-TA (0.25 mm×30 m, manufactured by Advanced Separation Technologies Inc., NJ, USA) was used for the above determination of optical purity. The gas chromatography analysis for optical isomers was carried out under the following conditions.

Conditions for analysis of methyl 4-chloro-3-hydroxybutyrate:

Column temperature: 110° C.; detector temperature: 200° C.; carrier gas: nitrogen; flow rate: 0.7 ml/min; detector: FI D; split ratio: 100/1. Retention time: 15.5 min (R-isomer); 16.3 min (S-isomer).

Conditions for analysis of 3-hydroxy-γ-butyrolactone:

Column temperature: 150° C.; detector temperature: 200° C.; carrier gas: nitrogen; flow rate: 0.7 ml/min; detector: FID; split ratio: 100/1. Retention time: 11.3 min (S-isomer); 12.0 min (R-isomer).

The physical properties of the obtained 3-hydroxy-γ-butyrolactone were well identical to the data described in "Synthetic Communications", 16(2), pp.183–190,1986.

$[\alpha]_D^{20}=-76.2°$ (c=1.95, EtOH)

$^1$H-NMR (CDCl$_3$, 250 MHz), δppm: 2.54 (d, 1 H, J=18 Hz); 2.79 (dd, 1 H, J=18 Hz, J=6 Hz); 3.29 (s, 1 H, OH); 4.34 (d, 1 H, J=10 Hz); 4.46 (dd, 1 H, J=10 Hz, J=4.5 Hz); 4.6–4.7 (m, 1 H);

$^{13}$C-NMR (CDCl$_3$), δppm: 177, 76.3, 67.2, 37.7

EXAMPLES 14 TO 32

A reaction was carried out by the same procedure as in Example 13 except that substrates shown in Table 3 were substituted for racemic methyl 4-chloro-3-hydroxybutyrate and Enterobacter sp. DS-S-75, Citrobacter freundii DS-S-13, Citrobacter freundii DS-K-40 and Bacillus sphaericus DS-ID-819 were used as the microorganism for each substrate. The determination as well as analysis for optical isomers of the various compounds thus obtained were also carried out by the same procedure as in Example 13. The yield and optical purity of the obtained compounds are shown in Table 3. The physical properties of the 3-hydroxy-γ-butyrolactone obtained in all these examples were identical to the data of Example 13.

The products and their yield in Examples 13 to 32 are shown in Table 3. The meaning of abbreviations in this table are as follows.

MH: Methyl 4-chloro-3-hydroxybutyrate
EH: Ethyl 4-chloro-3-hydroxybutyrate
IPH: Isopropyl 4-chloro-3-hydroxybutyrate
PH: Propyl 4-chloro-3-hydroxybutyrate
BH: Butyl 4-chloro-3-hydroxybutyrate
HL: 3-Hydroxy-γ-butyrolactone
No. 75: Enterobacter sp. DS-S-75
No. 13: Citrobacter freundii DS-S-13
No. 40: Citrobacter freundii DS-K-40
No. 819: Bacillus sphaericus DS-ID-819

TABLE 3

| Ex. | Strain | Substrate | Product (optical purity and yield) | |
|---|---|---|---|---|
| 13 | No. 75 | MH | R—MH >99% ee, 342 mg | S—HL 95.9% ee, 214 mg |
| 14 | No. 75 | EH | R—EH >99% ee, 304 mg | S—HL 92.4% ee, 214 mg |
| 15 | No. 75 | IPH | R—IPH >99% ee, 362 mg | S—HL 96.8% ee, 170 mg |
| 16 | No. 75 | PH | R—PH 96.6% ee, 374 mg | S—HL 96.6% ee, 164 mg |
| 17 | No. 75 | BH | R—BH >99% ee, 462 mg | S—HL 96.7% ee, 129 mg |
| 18 | No. 13 | MH | R—MH 72.5% ee, 419 mg | S—HL 93.7% ee, 169 mg |
| 19 | No. 13 | EH | R—EH >99% ee, 332 mg | S—HL 95.4% ee, 172 mg |
| 20 | No. 13 | IPH | R—IPH >99% ee, 382 mg | S—HL 94.4% ee, 160 mg |
| 21 | No. 13 | PH | R—PH >99% ee, 405 mg | S—HL 98.3% ee, 149 mg |
| 22 | No. 13 | BH | R—BH >99% ee, 409 mg | S—HL 96.5% ee, 136 mg |
| 23 | No. 40 | MH | R—MH 59.3% ee, 432 mg | S—HL 95.5% ee, 162 mg |
| 24 | No. 40 | EH | R—EH 98.3% ee, 354 mg | S—HL 95.3% ee, 187 mg |
| 25 | No. 40 | IPH | R—IPH >99% ee, 344 mg | S—HL 96.3% ee, 178 mg |
| 26 | No. 40 | PH | R—PH >99% ee, 431 mg | S—HL 98.4% ee, 136 mg |
| 27 | No. 40 | BH | R—BH >99% ee, 401 mg | S—HL 96.8% ee, 140 mg |
| 28 | No. 819 | MH | S—MH 91.9% ee, 306 mg | R—HL 42.0% ee, 136 mg |
| 29 | No. 819 | EH | S—EH >99% ee, 267 mg | R—HL 23.5% ee, 141 mg |
| 30 | No. 819 | IPH | S—IPH 94.5% ee, 320 mg | R—HL 65.5% ee, 83 mg |
| 31 | No. 819 | PH | S—PH 28.5% ee, 175 mg | R—HL 7.9% ee, 202 mg |
| 32 | No. 819 | BH | R—BH 31.1% ee, 222 mg | S—HL 4.8% ee, 179 mg |

According to the present invention, the optically active chlorohydrin and optically active 1,2-diol compound and/or optically active 3-hydroxy-γ-butyrolactone can be produced by using inexpensive materials with ease and on industrial scale, which comprises degrading one of the optical isomers of a racemic chlorohydrin compound of the formula [1] with a microorganism of the genus Pseudomonas (e.g. Pseudomonas sp. OS-K-29 or Pseudomonas sp. DS-K-NR818), the genus Enterobacter (e.g. Enterobacter sp. DS-S-75), the genus Citrobacter (e.g. Citrobacter freundii DS-S-13, Citrobacter freundii DS-K-40) as well as the genus Bacillus (e.g. Bacillus sphaericus DS-ID-819) and remaining an other optical isomer in the reaction system, and further dehalogenating only one of the optical isomers to convert into an optically active 1,2-diol compound or 3-hydroxy-γ-butyrolactone, and then recovering the remaining optically active chlorohydrin compound and the produced optically active 1,2-diol compound and/or optically active 3-hydroxy-γ-butyrolactone.

The optically active chlorohydrin compound and the optically active 1,2-diol compound and/or optically active 3-hydroxy-γ-butyrolactone which are obtained by the present invention are useful as intermediates for preparing medicaments, agricultural chemicals, physiologically active substances and ferroelectric liquid crystals. Especially, the optically active 4-chloro-3-hydroxybutyronitrile and the corresponding carboxylate (i.e. the optically active methyl 4-chloro-3-hydroxybutyrate and ethyl 4-chloro-3-hydroxybutyrate, etc.) which have a C4-structure are important as a precursor compound for preparing pharmaceutically useful compounds such as optically active carnitine, 4-chloro-3-hydroxybutanoic acid, 4-hydroxy -2-pyrrolidone and 1,2,4-butanetriol. Thus, the present invention can provide such important compounds inexpensively and conveniently and is very valuable from the industrial viewpoint.

What is claimed is:

1. A process for the optical resolution of a racemic chlorohydrin compound, which comprises treating a racemic mixture of a chlorohydrin compound of the formula:

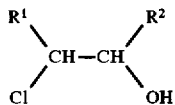

[1]

wherein $R^1$ is a hydrogen atom or a lower alkyl group and $R^2$ is (i) a substituted or unsubstituted lower alkyl group when $R^1$ is a hydrogen atom, provided that a hydroxymethyl group is excluded, or (ii) $R^2$ is a hydrogen atom when $R^1$ is a lower alkyl group, with a culture broth or cells of a microorganism, having an ability of selectively degrading one of the optically active isomers of the racemic chlorohydrin compound of the formula [1], selected from the group of bacterial genera consisting of Pseudomonas, Enterobacter, Citrobacter, and Bacillus, or a processed product of the cells, and thereby degrading, selectively, only one of the optically active isomers in the racemic mixture, the other optically active isomer remaining in the reaction system.

2. A process as claimed in claim 1, wherein the optically active chlorohydrin compound remaining in the reaction system is recovered.

3. A process as claimed in claim 2, wherein the racemic chlorohydrin compound is a compound of the formula [1] wherein $R^1$ is a lower alkyl group and $R^2$ is a hydrogen atom.

4. A process as claimed in claim 2, wherein the racemic chlorohydrin compound is a compound of the formula [1] wherein $R^1$ is a hydrogen atom and $R^2$ is a lower alkoxycarbonylmethyl group, and wherein the microorganism is Pseudomonas sp. OS-K-29, and thereby, an optically active 1,2-diol compound of the formula:

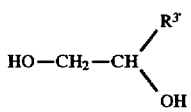

[2a]

wherein $R^{3'}$ is a lower alkoxycarbonylmethyl group, and further, an optically active 3-hydroxy-γ-butyrolactone of the formula:

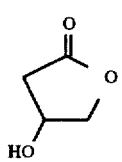

are produced in addition to the optically active isomer remaining in the reaction system.

5. A process as claimed in claim 4, wherein $R^{3'}$ is a member selected from the group consisting of methoxycarbonylmethyl, ethoxycarbonylmethyl, and isopropoxycarbonylmethyl.

6. A process as claimed in claim 2, wherein the racemic chlorohydrin compound is a compound of the formula [1] wherein $R^1$ is a hydrogen atom and $R^2$ is a lower alkoxycarbonylmethyl group, and the microorganism is a member selected from the group consisting of Pseudomonas sp. DS-K-NR 818, Enterobacter sp. DS-S-75, Citrobacter freundii DS-S-13, Citrobacter freundii DS-K-40, and Bacillus sphaericus DS-ID-819, and thereby an optically active 3-hydroxy-γ-butyrolactone of the formula:

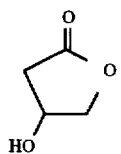

is produced in addition to the optically active isomer remaining in the reaction system.

7. A process as claimed in claim 6, wherein $R^2$ in the compound [1] is a member selected from the group consisting of methoxycarbonylmethyl, ethoxycarbonylmethyl, propoxycarbonylmethyl, isopropoxycarbonylmethyl, and butyloxycarbonylmethyl.

8. A process as claimed in claim 1, wherein the racemic chlorohydrin compound is a compound of the formula [1] wherein $R^1$ is a hydrogen atom and $R^2$ is a substituted or unsubstituted lower alkyl group.

9. A process as claimed in claim 8, wherein $R^2$ is a member selected from the group consisting of an ethyl group, a cyanomethyl group, a lower alkoxycarbonylmethyl group, and a lower alkoxymethyl group.

10. A process as claimed in claim 8, wherein $R^2$ is a lower alkoxycarbonylmethyl group.

11. A process as claimed in claim 10, wherein the microorganism is a bacteria of the genus Enterobacter, Citrobacter, or Bacillus.

12. A process as claimed in claim 10, wherein the microorganism is Pseudomonas sp. DS-K-NR 818.

13. A process as claimed in claim 8, wherein $R^2$ is a member selected from the group consisting of methoxycarbonylmethyl, ethoxycarbonylmethyl, and isopropoxycarbonylmethyl.

14. A process as claimed in claim 8, wherein the microorganism is Pseudomonas sp. OS-K-29.

15. A process as claimed in claim 14, wherein an optically active 1,2-diol compound of the formula:

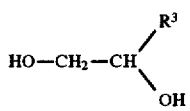

[2]

wherein $R^3$ is a substituted or unsubstituted lower alkyl group, is produced in addition to the optically active isomer remaining in the reaction system.

16. A process as claimed in claim 1, wherein the microorganism is a bacteria of the genus Pseudomonas, which has an ability of selectively degrading one of the optically active isomers of the racemic chlorohydrin compound of the formula [1].

* * * * *